United States Patent [19]

Wortrich

[11] Patent Number: 5,263,939
[45] Date of Patent: Nov. 23, 1993

[54] RETAINER FOR LAPAROSCOPIC CANNULA

[75] Inventor: Theodore S. Wortrich, Long Beach, Calif.

[73] Assignee: Surgin Surgical Instrumentation, Inc., Placentia, Calif.

[21] Appl. No.: 958,920

[22] Filed: Oct. 9, 1992

[51] Int. Cl.$^5$ .............................. A61M 5/32
[52] U.S. Cl. .................... 604/174; 604/180; 128/DIG. 26
[58] Field of Search ............ 604/174, 175, 176, 178, 604/179, 180; 128/DIG. 26; 606/151, 157, 158

[56] References Cited

U.S. PATENT DOCUMENTS

| | | |
|---|---|---|
| 2,402,306 | 6/1946 | Turkel . |
| 2,898,917 | 8/1959 | Wallace . |
| 3,123,074 | 3/1964 | Turner . |
| 3,487,837 | 1/1970 | Petersen . |
| 3,568,679 | 3/1971 | Reif . |
| 3,683,911 | 8/1972 | McCormick . |
| 3,721,229 | 3/1973 | Panzer . |
| 3,856,020 | 12/1974 | Kovac . |
| 3,893,446 | 7/1975 | Miller . |
| 3,918,446 | 11/1975 | Buttaravoli . |
| 3,926,185 | 12/1975 | Krzewinski . |
| 4,170,995 | 10/1979 | Levine et al. . |
| 4,333,468 | 6/1982 | Geist . |
| 4,380,234 | 4/1983 | Kamen .................... 604/180 |
| 4,393,873 | 7/1983 | Nawash et al. ............ 604/151 |
| 4,464,178 | 8/1984 | Dalton ..................... 604/174 |
| 4,516,968 | 5/1985 | Marshall et al. ........... 604/174 |
| 4,519,793 | 5/1985 | Galindo ................... 604/180 |
| 4,579,120 | 4/1986 | MacGregor ............... 604/174 |
| 4,593,681 | 6/1986 | Soni ....................... 604/174 |
| 4,645,492 | 2/1987 | Weeks .................... 604/174 |
| 4,650,474 | 3/1987 | Backer .................... 604/180 |
| 4,675,006 | 6/1987 | Hrushesky ................ 604/180 |
| 4,699,616 | 10/1987 | Nowak et al. ............. 604/180 |
| 4,717,385 | 1/1988 | Cameron et al. .......... 604/174 |
| 4,767,411 | 8/1988 | Edmunds ................. 604/180 |
| 4,915,694 | 4/1990 | Yamamoto et al. ........ 604/180 |
| 5,026,352 | 6/1991 | Anderson ................. 604/174 |
| 5,069,206 | 12/1991 | Crosbie ................... 604/174 |
| 5,073,169 | 12/1991 | Raiken .................... 604/174 |
| 5,137,520 | 8/1992 | Maxson et al. ............ 604/180 |
| 5,176,648 | 1/1993 | Holmes et al. ............ 604/164 |

FOREIGN PATENT DOCUMENTS

| | | | |
|---|---|---|---|
| 653436 | 11/1937 | Fed. Rep. of Germany | 604/174 |
| 1184139 | 10/1957 | France ................. | 604/174 |
| 2072511 | 10/1981 | United Kingdom ...... | 604/174 |

*Primary Examiner*—John G. Weiss
*Attorney, Agent, or Firm*—Merchant, Gould, Smith, Edell, Welter and Schmidt

[57] ABSTRACT

A cannula retaining device is disclosed in which a base includes a sleeve in the center thereof to provide a port for insertion of a cannula. A clamp including a compressible plug with an interior aperture that matches the diameter of the cannula is fitted into the base. The clamp includes a pair of laterally extending finger engageable arms which tighten the compressible plug on the cannula, thereby receiving the cannula while allowing adjustment, angulation and rotation.

16 Claims, 4 Drawing Sheets

RETAINER FOR LAPAROSCOPIC CANNULA

BACKGROUND OF THE INVENTION

1. Field of Invention

This invention relates in general to a retention device that prevents a cannula from becoming dislodged from the operative site during surgery. More particularly, this invention relates to a disposable retaining base providing secure attachment to the patient and facilitating the installation, substitution and adjustment of cannulae and instruments used in laparoscopic surgery.

2. Description of Related Art

Laparoscopic surgery is a recently introduced method for performing various types of surgical operations. Unlike other types of surgical procedures, laparoscopic surgery does not require large incisions to expose the internal organs. Typical laparoscopic procedures begin with the creation of a pneumoperitoneum (inflated peritoneum) in order to safely insert instruments into the body cavity. A small hole is first cut through the body wall and a tubular sheath or cannula is inserted through the hole. The body cavity is then distended by filling the body cavity with gas under pressure. Other cannulae are subsequently inserted into the body cavity to form housings for the insertion of various surgical instruments. For example, a laparoscope may be inserted through a cannula so that the surgeon can study ("visualize") the internal organs. Also, other types of surgical instruments may be inserted through these cannulae so that the surgery can be performed while the organs are being visualized and manipulated during the surgery.

There is often a need to restrain the instruments within the cannula to minimize excess movement, and a separate need to prevent excessive movement of the cannula itself, while allowing specific types of movement. If the cannula shifts through the incision as the surgeon carries out the operation, the laparoscope or other instruments may shift to affect the procedure or distract the surgeon and interfere with the operation. In addition, if a cannula becomes dislodged during the surgery, the distention of the body cavity may be lost. Both the re-establishment of the pneumoperitoneum and the re-insertion of the cannula prolong the length of the surgical procedure.

In addition there is often a need to adjust the position of the cannula or to adjust the angle of the cannula with respect to the patient's body without causing any unwanted shifting of the cannula. Such motion allows the surgeon to view other parts of the organs or to manipulate instruments relative to the organs during the surgery. Sometimes the cannula is made of material which is not treated with a special spiral retention device or is treated with a non-sticking material such as teflon. In such cases, special configurations or materials are needed to address these types of cannulae.

It is therefore desirable for the surgeon to have the cannula remain in proper position within the patient without the need to manually hold it in place thereby minimizing delays in such surgical procedures. It is also desirable to permit the hands of the surgeon to be kept free so that the surgeon may direct attention to other cannulae or other surgical needs. Therefore, ease of adjusting the retention force with the fingers of a single hand and placement of the trocar within the cannula is also an objective. Since various manufacturers make different sized cannulae, it is also desirable for cannulae retaining devices to be adaptable to different diameter cannulae.

In addition, it is sometimes desirable during a laparoscopic procedure to change the angle at which the cannula enters the body cavity in order to view different portions of the internal organs or to maneuver the other surgical instruments. However, such angulation can place excessive stress on the adhesive and cause it to separate. Thus, it is desirable to facilitate flexible but secure support a cannula in such a manner so that the angle can be changed with respect to the patient's body without causing any unwanted shifting of the cannula or enlargement of the peritoneum while insuring that minimum stress is placed upon the mounting pad and adhesive.

Finally, it is desirable to provide some gas sealing to prevent, or at least minimize, the escape of the gas around the incision through which the cannula is inseted.

SUMMARY OF THE INVENTION

To overcome the limitations in the prior art described above, and to overcome other limitations that will become apparent upon reading and understanding the present specification, the present invention discloses a disposable cannula retaining device for laparoscopic surgical procedures.

A feature of the present invention is a disposable retaining device which is held in place in order to secure a cannula. The integration of an anchored base with a locking ratchet disposed above the insertion point ensures that the cannula will not be dislodged from the operative site but enables placement, securement and adjustment of the cannula.

The retaining device has a base for securing a cannula to the patient and a clamping mechanism for receiving the cannula while allowing adjustment, angulation and rotation.

A more specific example of a device in accordance with the present invention is a flat flexible base having a flexible neck that allows the inserted cannula to be tilted at any desired angle, a clamp which rotates around the neck of the base which can easily be tightened to hold the inserted cannula, and an pre-sized insert which snaps into the clamp and has an inner diameter that matches the diameter of the cannula being used.

A second example of a device in accordance with the present invention is a flat flexible base having a flexible neck, a clamp which rotates around the neck of the base having an integral inner portion with a central vertical aperture pre-sized to receive a cannula. The clamp further has a locking mechanism that compresses the integral inner portion thereby diminishing the inner diameter of the aperture.

Alternative examples of a device in accordance with the present and incorporating the features discussed above may also have a base having a bellowed neck which also allows the inserted cannula to be tilted at any desired angle. Finally, the features of the base, the clamp and the insert as discussed above may be wholly integral.

BRIEF DESCRIPTION OF THE DRAWINGS

Referring now to the drawings in which like reference numbers represent corresponding parts throughout.

DETAILED DESCRIPTION OF THE INVENTION

The present invention in this exemplification is a retaining device for a cannula used during laparoscopic surgical procedures. A pneumoperitoneum is usually created first to distend the peritoneum and allow greater freedom of movement in the cavity. An incision is made using a verres needle. The verres needle incorporates a cutting trocar and an obturator on the inside of the trocar. The obturator has a small axial hole for channeling gas through the verres needle to the insertion end. The obturator pushes out so that the trocar does not slice an internal organ. Once the verres needle is inserted into the body cavity, gas is pumped into the body cavity to establish the pneumoperitoneum. The verres needle is then removed and an optical port is created by inserting a cannula into the original incision using one of several methods incorporating the retaining device in accordance with the present invention.

In a first method, an optical port is created using a cannula and trocar. The surgeon selects the puncture site and places the retaining device so that the puncture site is visible through the opening in the neck of the base. The cannula and the trocar are inserted through the aperture in the retaining device and into the patient to create the port. The trocar is removed and the cannula is moved into a desired position. The clamp is then tightened to maintain the cannula position relative to the base and the patient. Pressurized gas is then pumped into the body cavity through the cannula to distend the body cavity. Finally, a laparoscope is inserted through the optical port cannula and into the body cavity.

In an alternative method, the retaining device is attached to the upper end of the cannula and trocar. Then the cannula and trocar are inserted into the body cavity of the patient as described above. The retaining device is then slid down the cannula and attached to the patient. The trocar is removed and the cannula is moved nto a desired positioned. The clamp is then tightened to maintain the cannula position relative to the base and the patient. Pressurized gas is then pumped into the body cavity through the cannula to distend the body cavity and the laparoscope is inserted through the optical port cannula and into the body cavity.

These procedures are repeated as needed to create the desired number of ports. The retention of the cannula allows instruments to be manipulated through the cannula without dislodging the cannula from the pneumoperitoneum due to friction between the instruments and the cannula and consequently causing the loss of the pneumoperitoneum. Once the pneumoperitoneum is lost, the surgeon must stop the procedure and re-establish the pneumoperitoneum thus prolonging the length of the surgical procedure.

Figure 1:
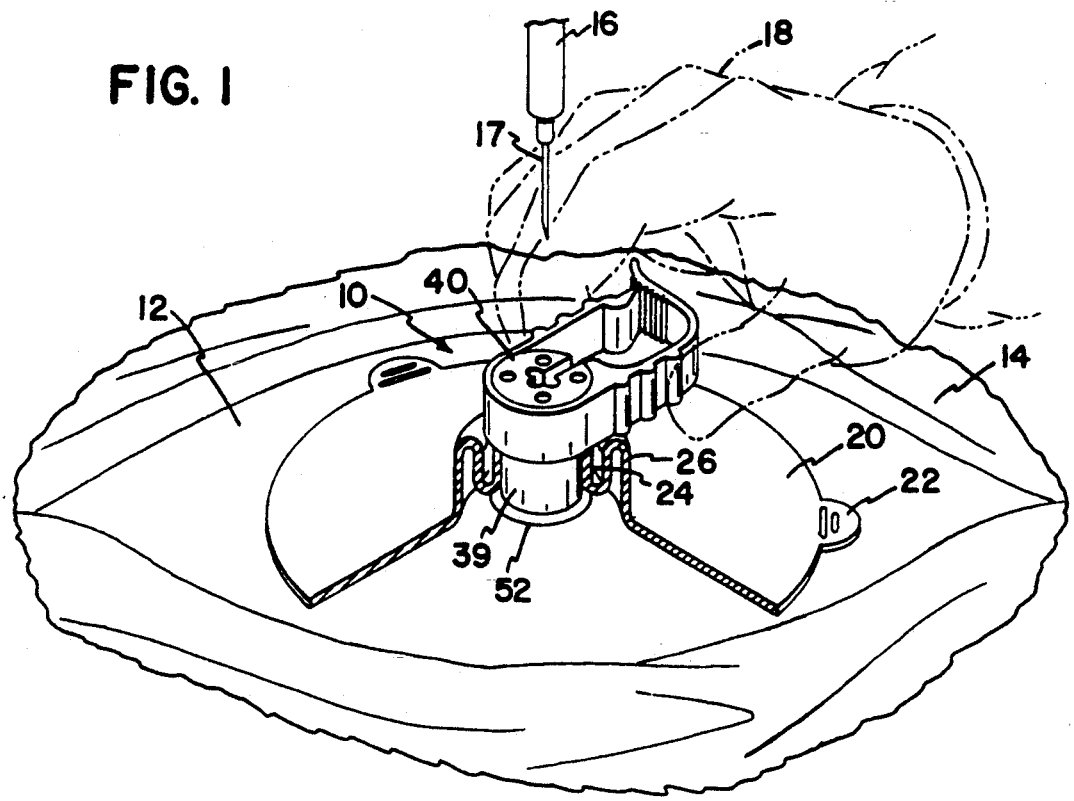
FIG. 1 is a view of a portion of an operating room environment during a laparoscopic surgical procedure and showing a device in accordance with the invention in perspective, with adjacent cannula and trocar.

Refer now to FIG. 1, which illustrates the present invention as used in an operating room environment during a laparoscopic surgical procedure. A cannula retaining device 10 is shown attached to a patient 12 prepared for laparoscopic surgery and partially covered with sterile drapery 14. According to one particular method of using the retaining device, a cannula 16 having a trocar 17 inserted therein is aligned with the retaining device 10 and prepared for insertion while the surgeon grasps the retaining device 10 with two fingers (illustrated in outline) 18 to clamp the cannula once the cannula is positioned into the body cavity.

Figure 2:
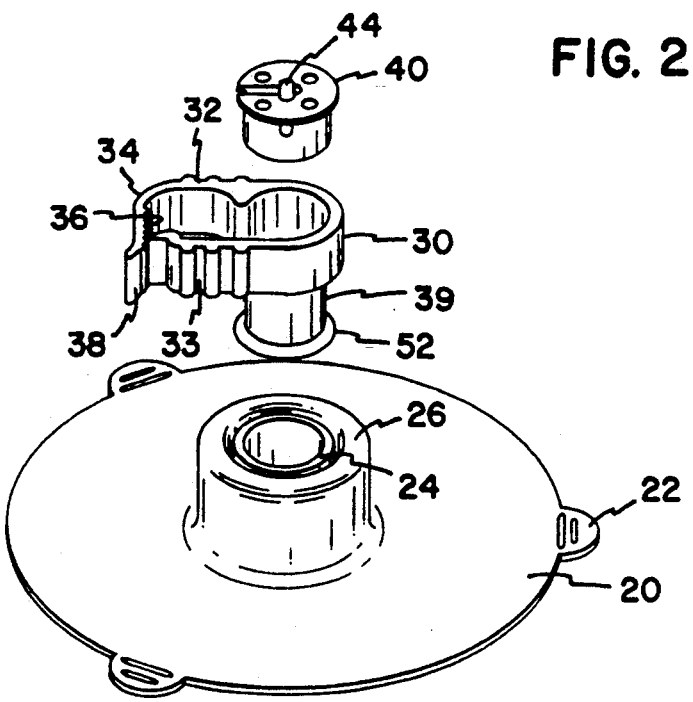
FIG. 2 is an exploded view of the cannula retainer device in accordance with the invention showing the base, the clamping device and the insert

FIG. 2 illustrates the elements of the retaining device 10. The retaining device 10 comprises a base 20, a retaining clamp 30, and an insert 40. A substantially round base 20 is shown having tabs 22 along the edges of the base 20 for facilitating removal upon completion of the surgical procedure. At the center of the base 20 is a neck 24 through which the cannula protrudes. On the base 20 surrounding the neck 24 are one or more concentric relief folds 26. These relief folds 26 allow the neck and cannula to be angulated from its relative perpendicular position without transmitting a sheering strain on the base 20. Thus, the relief folds 26 allow a more natural movement. On the underside of the base 20, an adhesive backing or vacuum secures the base to the patient thereby ensuring that the pneumoperitoneum is maintained.

A cannula 16 is grasped by an insert 40 which can be separate from the clamp 30 or can be made an integral part of the clamp 30. Since cannulae 16 can be made of material which is not treated with a special spiral retention device, is of a different shape or may be treated with a non-sticking material such as teflon, special inserts 40 are sometimes required. In these special circumstances, the inserts 40 need to be designed to address the special configuration of the cannula 16 or made of a soft sticker material such as silicone in order to securely grasp the cannula 16. In such instances, the clamp 30 and the insert 40 would be fabricated from different materials and therefore the insert 40 needs to be separate from the clamp 30.

Figure 5:
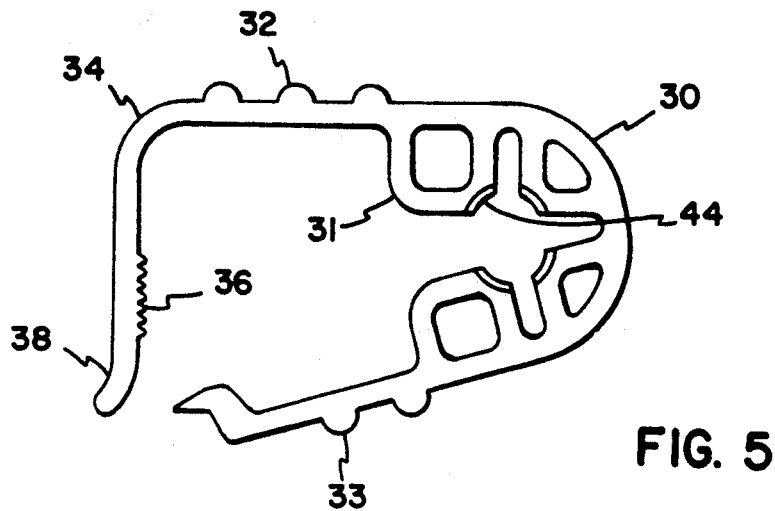
FIG. 5 is a top view of a retaining clamp in accordance with the invention having a narrow aperture for receiving a cannula.
Figure 6:
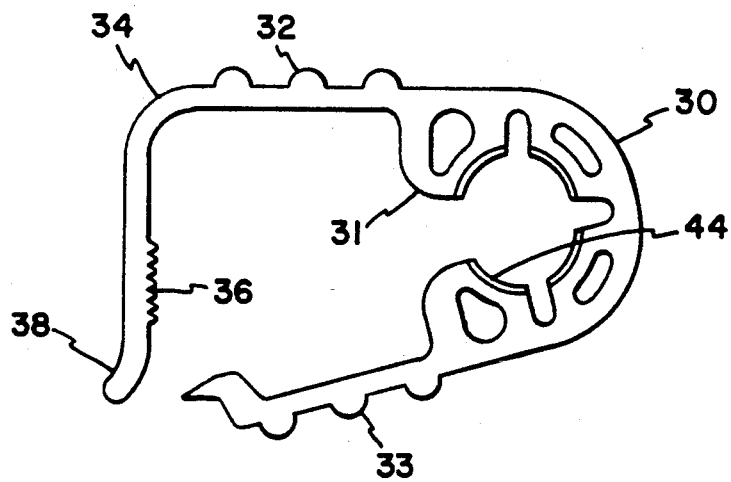
FIG. 6 is a top view of a retaining clamp in accordance with the invention having a broad aperture for receiving a cannula.

FIG. 2 illustrates an insert 40 separate from the clamp 30. The insert 40 is a short, substantially cylindrical sleeve having an inner surface 44 for grasping a cannula 16. Inserts 40 of varying inner diameter 44 can be selected to match different size cannulae 16. The pre-sized insert 40 fits into a clamp 30 and is chosen to match the diameter of the cannula 16 being used. The insert 40 snaps easily into the clamp 30 and a lip 42 is formed around the upper edge of the insert that rests upon the upper edge of the clamp 30 when inserted. FIGS. 5 and 6 illustrate the alternative design where the insert 40 is integral with the clamp 30. In any event, the insert 40 or the integral insert/clamp arrangement is color coded according to the diameter of the inner aperture 44.

Figure 3:
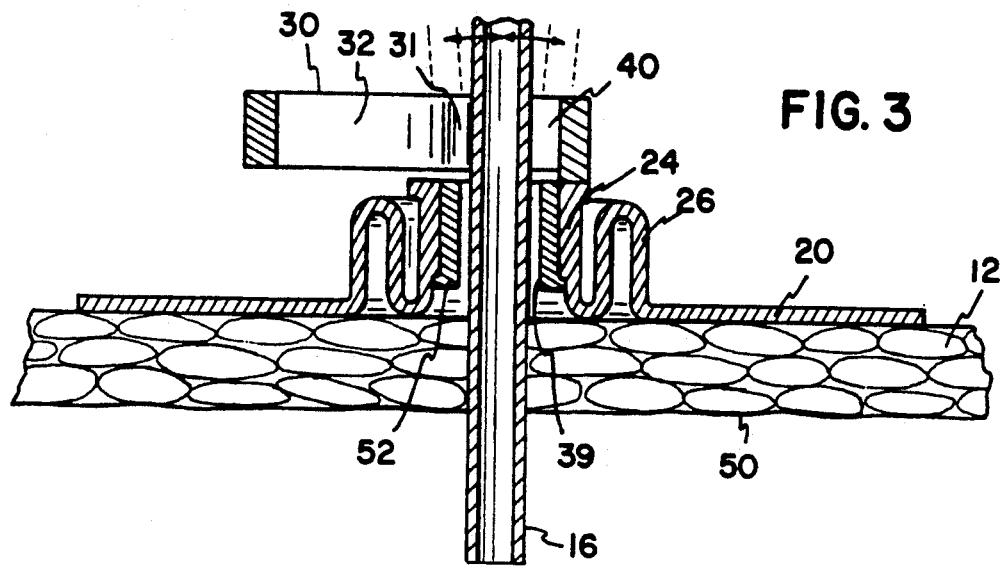
FIG. 3 is a side sectional view of a device in accordance with the invention attached to a patient showing the base, retaining clamp and insert, with a cannula inserted through the device.
Figure 4:
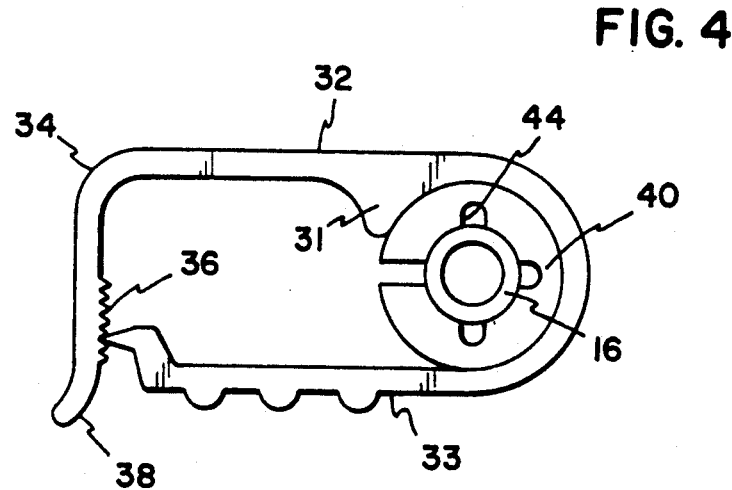
FIG. 4 is a top view in accordance with the invention showing the base, retaining clamp and insert.

FIG. 3 illustrates the cannula 16 positioned inside the body cavity 50 through a retaining device 10 attached to a patient 12. The cannula 16 is shown grasped by the insert 40 and clamp 30. FIG. 4 illustrates a top view of an insert 40 snapped into place inside a clamp 30 and a cannula 16 secured therein. Now referring to FIGS. 4-6, two arms 32, 33 are shown extending outward tangently from the clamp 30 to form the locking rachet. The first arm 32 of the clamp 30 bends toward the second arm 33 forming an L-bend 34 and receives the end portion of a second arm 33 in teeth 36 disposed at the end of the L-shaped first arm member 32 upon the inside surface thereof. Thus the second arm 33 is engaged in the teeth 36 of the first arm 32 when the clamp 30 is tightened. The clamp 30 may be tightened by using only the thumb and forefinger to press the second arm 33 toward the first arm 32. The second arm 33 is therefore ratcheted over the teeth 36 of the first arm 32 and thus decreases the diameter of the cannula receiving surface 44. The receiving arm 32 has a tab 38 which allows the rigid arm 32 to be pulled away from the cylindrical sleeve with a single hand thus disengaging the second arm 33 from the teeth 36 of the first arm 32. The second arm 33 then springs back into the released position.

Figure 7:
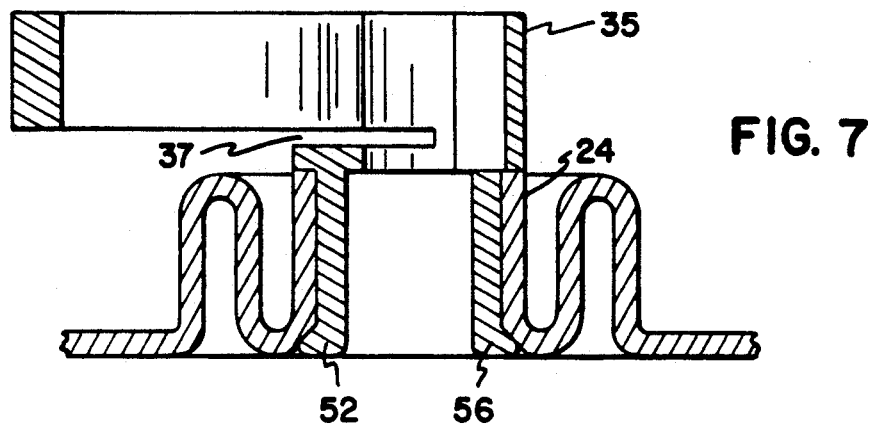
FIG. 7 is a side sectional view in accordance with the invention showing the base, retaining clamp and insert.

FIG. 7 shows the arms 32, 33 extending from the clamp 30 and illustrates a slit 37 between the arms 32, 33 and the depending tube portion 39 of the clamp 30, such that the inner diameter of the cannula receiving surface 44 is decreased when finger pressure is applied to the sides of the arms 32, 33. The insertable end 39 of the clamp 30 is smaller in diameter than the locking rachet end 35 of the clamp 30. The locking ratchet end 35 has an opening 31 longitudinally along one of the sides that allows the diameter of the inner surface 44 to be decreased when the clamp 30 is tightened. A lip 52 circumscribes the edge of the depending tube portion 39 of the clamp 30. The lip 52 secures the clamp 30 against the neck 24 of the base 20 by snapping into the receiving groove 56 on the inner surface of the neck 24 of the base 20. The seating of the clamp 30 into the neck 24 facilitates angulation of the neck 24 of the base 20. In addition, this configuration allows the clamp 30 to rotate around the neck 24 of the base 20 for proper positioning and thereby promotes superior angular tilting of the cannula 16 by ensuring that the arms 32, 33 of the clamp 30 are out of the line of angulation.

Figure 8:
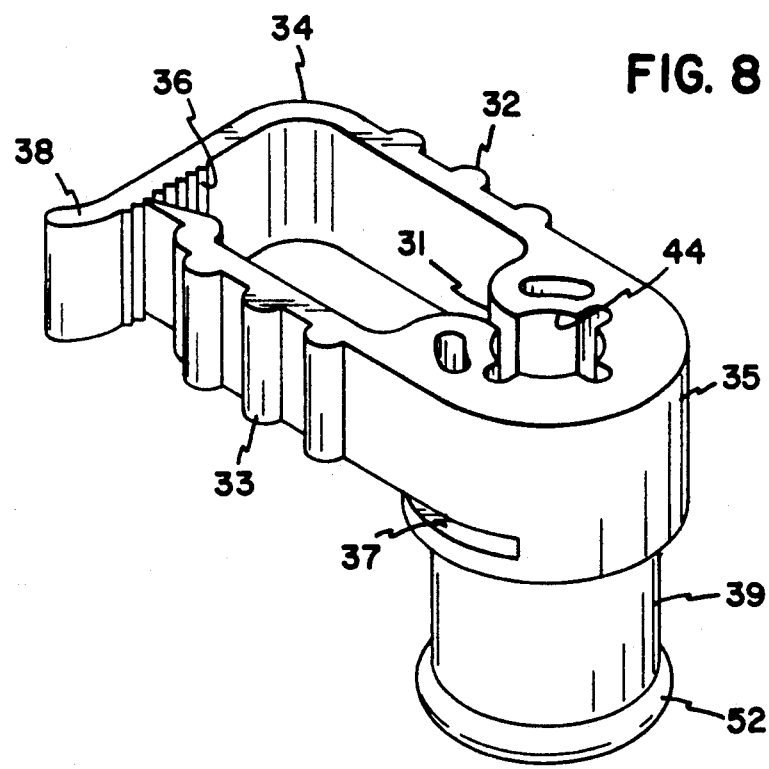
FIG. 8 is perspective view of a retaining clamp in accordance with the invention.

FIG. 8 is a prospective view of the clamp 30 as described above and also illustrated in FIGS. 5 and 6. The two arms 32, 33 are shown extending outward tangently from the clamp 30. Beneath the point where the arms 32, 33 extend outward from the cylindrical tube portion 35 of the clamp 30, the slit 37 that enables the inner diameter 44 of the clamp 30 to be decreased is observable. As described above, the lip 52 which circumscribes the edge of the depending tube portion 39 of the clamp 30 is also illustrated.

In summary, a low cost, disposable cannula retaining device has been described. Because of these features, the cannula is maintained in place and the time required to complete surgical procedures is reduced.

The preceding description of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A cannula retaining device, comprising:
   a substantially flat base including a cylindrical hollow sleeve about a central axis, through which a cannula means can be inserted; and
   clamp means registering in the hollow sleeve and including compressible means having a cannula receiving clamp aperture about the cannula axis, the clamp means further including engageable arm means extending perpendicularly to the axis for selectively compressing the compressible means.

2. A device as set forth in claim 1 above, wherein the clamp means comprise a pair of arms having terminal portions including releasable means for locking in different positions of engagement.

3. A device as set forth in claim 2, wherein the base is of a flexible material which readily conforms to the surface contour of the patient, and includes a sinuous region intercoupling the base and the sleeve for permitting angulation of an inserted cannula.

4. A device as set forth in claim 2 above, wherein the clamp means comprises a unitary device having a compressible plug with a cannula receiving aperture extending arms integral with the plug and including end engagement means, the arms extending laterally to the axis, and being resilient to maintain compression when engaged.

5. A device as set forth in claim 2 above, wherein the clamp means comprises a clasp having a pair of arms extending from a common curved section defining a clamp aperture about the axis, and a substantially open loop section laterally extending therefrom, the arms terminating in releasable locking means, and the device further including a compressible cannula receiving plug in the aperture.

6. A device as set forth in claim 2 above, wherein the clamp means comprises a depending tube about the axis, the tube fitting as a male member into the hollow sleeve, a pair of resilient laterally extending arms disposed at a superior end of the tube and integrated therewith, one of the arms having a terminal portion including ratchet teeth and the other arm having a tooth engaging end.

7. A device as set forth in claim 6, wherein the device further comprises common curved section about the axis, a first arm extending tangentially from the common curved section and second arm extending tangentially from an opposite side of the common curved section substantially parallel to the first arm, the first arm having an L-shaped end region terminating in an extending tab, and ratchet teeth along the end of an inner portion of the L-shaped end region, and wherein the second arm includes an end tooth for engaging in the ratchet teeth on the first arm.

8. A device as set forth in claim 7, wherein the device further comprises compression means defining a slit between the arms and a principal portion of the depending tube, such that the inner diameter of the common curved section is decreased when finger pressure is applied to sides of the arms.

9. A cannula retaining device for use in laparoscopic and other applications, comprising:
   a body attachment member having a seating flange and an integral cylindrical sleeve extending outwardly therefrom;
   clamp means including a depending hollow cylinder mating within the inner wall of the sleeve, and a open upper locking loop integral with the clamp means; and a cannula retainer disposed within a wall portion of the clamp means.

10. A device as set forth in claim 9 above, wherein the body attachment member includes sinuous means at the region of juncture of the sleeve to the flange.

11. A device as set forth in claim 9 above, wherein the clamp means further comprises means for securing the locking loop at different positions of closure with a varying diameter wall portion being defined thereby to compress the cannula retainer.

12. A device as set forth in claim 9 above, wherein the retainer further comprises means defining a central vertical aperture sized to receive a cannula, whereby the axial orientation of the cannula can be varied without weakening securement at the attachment member and adjustments in the position of the cannula can be made.

13. A device as set forth in claim 9 above, wherein the cannula retainer is integral with the clamp means.

14. A device as set forth in claim 9 above, wherein the cannula retainer is separate from the clamp means.

15. A cannula retaining device for use in laparoscopic and other applications, comprising:
a body attachment member having a seating flange and an integral cylindrical sleeve extending outwardly therefrom about a desired axis, the member including sinuous means at the region of juncture of the sleeve to the flange, the sleeve further comprising an inner wall of predetermined dimensions;
clamp means including a depending hollow cylinder mating within the inner wall of the sleeve, and a open upper locking loop integral therewith extending transversely relative to the axis, and having means for securing the loop at different compression positions with a varying diameter wall portion being defined thereby; and
a cannula retainer of pliable material disposed within the wall portion of the clamp means, the retainer having a central vertical aperture sized to receive a cannula, whereby the axis, rotational and angular orientations of the cannula can be varied without weakening securement at the attachment member.

16. A device for enabling securement and manipulation of a cannula penetrating a body wall along a cannula axis, comprising:
a support member having a pad for adhesive attachment to the body area about the cannula penetration area, the support member including a flexible base and an upstanding sleeve about the penetration area;
a clasp member having a compressible loop-shaped body comprising a wall defining a substantially circular arc segment and a pair of spaced-apart arms having end engagement means, the clasp member being resiliently deformable and compressible to different positions to diminish the arc segment, the clasp member further including a depending tubular sleeve member rotatable within a female sleeve member; and
resiliently compressible cannula retainer means having a central aperture size to receive the cannula and fitting within the arc segment of the clasp member such that the cannula is retained when the arms are engaged at their ends, wherein one arm has an L-shaped terminal segment and teeth along the base of the L and the other arm has an offset end configured to engage in the teeth such that the clasp can be tightened/compressed to a desired degree by inward flexure at the arms and released by outward bending of a tip of the L-shaped segment.

* * * * *